United States Patent [19]

Landis

[11] Patent Number: 5,413,726
[45] Date of Patent: May 9, 1995

[54] PHOSPHITE ADDUCT OF A TELOMERIZED VEGETABLE OIL FOR LUBRICANT COMPOSITIONS

[75] Inventor: Phillip S. Landis, Alexandria, Va.

[73] Assignee: International Lubricants, Inc., Seattle, Wash.

[21] Appl. No.: 62,828

[22] Filed: May 14, 1993

Related U.S. Application Data

[60] Division of Ser. No. 775,188, Oct. 11, 1991, Pat. No. 5,229,023, which is a continuation-in-part of Ser. No. 596,820, Oct. 12, 1990, abandoned.

[51] Int. Cl.$^6$ ............... C10M 159/12; C10M 137/00; C07F 9/02
[52] U.S. Cl. ................... 252/49.8; 558/159; 558/161; 558/163; 558/180
[58] Field of Search ............... 558/159, 161, 163, 180; 252/49.8

[56] References Cited

U.S. PATENT DOCUMENTS

| | | | |
|---|---|---|---|
| 3,105,819 | 10/1963 | Anderson | 558/161 |
| 4,587,107 | 5/1986 | Wisniak | 252/49.8 |
| 4,925,581 | 5/1990 | Erickson et al. | 252/49.8 |
| 5,023,312 | 6/1991 | Erickson et al. | 252/49.8 |
| 5,229,023 | 7/1993 | Landis | 252/57 |
| 5,262,074 | 11/1993 | Erickson et al. | 252/49.8 |
| 5,282,989 | 2/1994 | Erickson et al. | 252/49.8 |
| 5,302,305 | 4/1994 | Jolley et al. | 558/180 |

Primary Examiner—Jerry D. Johnson
Attorney, Agent, or Firm—Davis Wright Tremaine

[57] ABSTRACT

There is disclosed a group of lubricant additives that have improved oxidative stability, high viscosity and relatively lower cost and that comprise telomerized vegetable oils having no more than 4% polyunsaturated fatty acids. There is also disclosed sulfurized and phosphite adduct derivatives of telomerized vegetable oil for use as lubricant additives.

5 Claims, 1 Drawing Sheet

PHOSPHITE ADDUCT OF A TELOMERIZED VEGETABLE OIL FOR LUBRICANT COMPOSITIONS

CROSS-REFERENCE TO RELATED APPLICATIONS

This application is a divisional application of U.S. patent application No. 07/775,188, filed Oct. 11, 1991, now U.S. Pat. No. 5,229,023, which is a continuation-in-part of U.S. patent application Ser. No. 596,820, filed Oct. 12, 1990, now abandoned.

TECHNICAL FIELD OF THE INVENTION

The present invention relates to lubricant compositions and lubricant additives comprising telomerized vegetable oil. More specifically, this invention relates to telomerized vegetable oil wherein the vegetable oil is a triglyceride having fatty acid side chains predominantly from about 16 to about 26 carbon atoms in length and at least one double bond. This invention further relates to methods for using a telomerized vegetable oil in a lubricant additive or a lubricating composition and to methods for telomerizing vegetable oil.

BACKGROUND OF THE INVENTION

Lubricants are widely used to reduce friction between surfaces of moving parts and thereby reduce wear and prevent damage to the surfaces and parts. Lubricants are composed principally of a base stock and a lubricant additive. The base stock is generally a relatively high molecular weight hydrocarbon. In applications where there is a large amount of pressure applied to moving parts, lubricating compositions composed only of hydrocarbon base stock tend to fail and the parts become damaged. This problem has been addressed by adding materials (i.e., lubricant additives) to the lubricating composition to increase high pressure performance. Such additives are called "extreme pressure additives." Examples of extreme pressure additives are sulfurized sperm whale oil and sulfurized jojoba oil. There is a continuing need in the art to find alternate extreme pressure additives because sperm whale oil is no longer available due to an international ban and jojoba oil is expensive and in short supply.

Extreme pressure additives prevent destructive metal-to-metal contact in lubrication at high pressure and/or temperature such as that found in certain gear elements in automotive vehicles and various industrial machines where high pressure can cause a film of lubricant to rupture. Extreme pressure/anti-wear lubricants should have good lubricity, good cooling properties, high film strength, good load bearing abilty, and miscibility with the usual types of base oils.

To make lubricants, such as motor oils, transmission fluids, gear oils, industrial lubricating oils, metal working oils, etc., one starts with a lubricant grade of petroleum oil from a refinery, or a suitable polymerized petrochemical fluid. Into this "base stock" is blended small amounts of specialty chemicals that enhance lubricity, inhibit wear and corrosion of metals, and retard damage to the fluid from heat and oxidation.

Anti-wear agents, extreme pressure agents and friction modifiers have been developed that are generally organic or organometallic compounds containing halogens, sulfur, phosphorus, or a combination of the three. Halogens have noted low-temperature metal-coating activity but can cause serious corrosion problems at the higher operating temperatures of modern vehicles or industrial machinery and have environmental problems upon disposal. Manufactures have, therefore, switched to derivatives of sulfur and phosphorus for lubricant additives.

Before 1972, lubricant additives were based on raw and chemical derivatives of sperm whale oil, a monoester of monounsaturated fatty acid chains. Replacement additives include phosphorized lard oils, sulfurized polyisobutylene and moderate molecular weight polymers. These additives have met with limited success. Better lubricating properties (i.e., friction and reduced wear) have been achieved with a natural wax ester, such as jojoba oil. Lubricant additives using jojoba oil have been described in U.S. Pat. No. 4,873,008, the disclosure of which is incorporated by reference herein. Jojoba oil suffers from limited availability and high cost.

Synthetic wax esters can be made by esterifying an unsaturated fatty acid and an unsaturated fatty alcohol. Synthetic wax ester can be sulfurized. Sulfurized wax esters often display excellent lubricating properties. However, the cost of a process to create and isolate a synthetic wax ester is extremely high and comparable with the cost of natural wax ester.

One solution to this problem is described in U.S. Pat. No. 4,970,010, the disclosure of which is incorporated by reference herein. This patent describes a group of sulfurized derivatives of triglyceride vegetable oil that achieve acceptable lubricating properties. However, processing costs are still relatively high because this process requires the presence of at least 25% wax ester and preferably, 50% wax ester. For practical applications, synthetic wax esters have to be derived from natural vegetable triglycerides, such as rapeseed oil or corn oil. Cost-adding conversion steps to a synthetic wax ester make synthetic wax esters relatively uneconomical for use as lubricant additives.

Liquid wax esters are formed by forming an ester bond between the functional groups of an unsaturated fatty acid and an unsaturated fatty alcohol. Liquid wax esters have been made from triglyceride rapeseed oil, such as a high erucic acid rapeseed (HEAR) oil by a complex and expensive process, such as is described in Bell, U.S. Pat. No. 4,152,278. HEAR oil is a triglyceride in its native form. Synthetic wax ester made from HEAR oil is a substitute for sperm whale oil or a natural wax ester, such as jojoba oil.

Synthetic wax esters can be made into phosphorous or sulfurized derivatives to improve friction, wear and extreme-pressure properties of a fluid. For example, sulfurized vegetable oil wax esters are described in U.S. Pat. No. 4,152,278 and phosphite adducts of synthetic vegetable oil wax esters are described in U.S. Pat. No. 4,970,010.

Although the supply of HEAR is more stable than the supply and availability of jojoba oil, the process of transforming a triglyceride oil into a mono-ester form is a difficult and expensive process with little, if any, cost advantage over jojoba oil. Thus, there is a need in the art to be able to use a vegetable triglyceride oil directly as a lubricant additive or as a derivative to eliminate the expensive conversion steps into a synthetic wax ester and retain the advantage of low cost and availability.

Triglyceride vegetable oils, such as HEAR, contain 10%–25% polyunsaturated fatty acids and are rich in longer chain (20–24 carbon atom) fatty acids. Dienic (two double bonds) fatty acids and trienic (three double bonds) fatty acids in a triglyceride oil are more reactive than monoenic (single double bond) fatty acids. Double bonds in a vegetable oil triglyceride, when used directly in a high temperature oxidizing environment, such as a lubricant additive, are attacked by oxygen and heat which causes the triglyceride to darken, thicken and lose solubility within lubricating oil base stocks. These undesirable properties limit the usefulness of triglyceride vegetable oils for lubricant additives. Therefore, there is a further need in the art to find an inexpensive processing means to improve the lubricating properties and characteristics of triglyceride oils for use as lubricant additives. This invention was made to satisfy those needs.

SUMMARY OF THE INVENTION

The present invention relates to telomerized triglyceride vegetable oils, sulfurized and phosphorus derivatives of telomerized triglyceride vegetable oils, and combinations thereof for use as lubricant additives, thermal oxidative stability enhancers and viscosity improvers. The invention further relates to telomerized triglyceride vegetable oils as a lubricating composition base stock substitute. Further still, this invention provides a process to telomerize triglyceride vegetable oils, wherein the telomerized vegetable oils have a lower iodine number than the vegetable oil before telomerization, increased viscosity, and no more than 4% of the fatty acids of the telomerized vegetable oil are polyunsaturated. The telomerized vegetable oil is further characterized by having aliphatic rings connecting fatty acids from different triglyceride molecules or from the same triglyceride molecule.

The telomerized vegetable oil of the present invention comprises no more than 4% polyunsaturated fatty acids and is polymerized, having aliphatic rings connecting triglyceride molecules. The telomerized vegetable oil is produced by a process comprising heating a triglyceride vegetable oil in a non-oxidizing atmosphere for at least 5 hours at a temperature of from about 200° C. to about 400° C. Traces of water in the form of water vapor facilitate the telomerization process and act as a catalyst for the telomerization reaction. The triglyceride vegetable oil has from about 10% to about 75% polyunsaturated fatty acids and fatty acid chains of from about 16 to about 26 carbon atoms in length. Preferably the vegetable oil is a mixture of a lower polyunsaturated vegetable oil such as rapeseed oil and a higher polyunsaturated vegetable oil, such as corn oil or safflower oil.

The present invention further comprises phosphite and sulfurized derivatives of telomerized vegetable oil. A phosphite adduct of telomerized vegetable oil comprises a mono-, di-, tri-, tetra-, penta-, or hexa-adduct of a reaction product of:

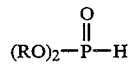

and a telomerized vegetable oil, wherein R is selected from the group consisting of H, $C_{1-12}$ alkyl, $C_{1-12}$ alkaryl, $C_{1-12}$ aralkyl, and cyclo $C_{4-8}$ alkyl. Preferably, R is selected from the group consisting of H, $C_{4-8}$ alkyl, $C_{4-8}$ alkaryl, $C_{4-8}$ aralkyl, and cyclo $C_{4-8}$ alkyl. A sulfurized derivative of telomerized vegetable oil comprises from about 5% to about 15% sulfur mixed with telomerized vegetable oil.

Lastly, the present invention comprises lubricant additives and lubricating compositions that comprise at least one component selected from the group consisting of a telomerized vegetable oil as described herein, a phosphite adduct of telomerized vegetable oil and sulfurized and telomerized vegetable oil.

DETAILED DESCRIPTION OF THE INVENTION

Figure 1:
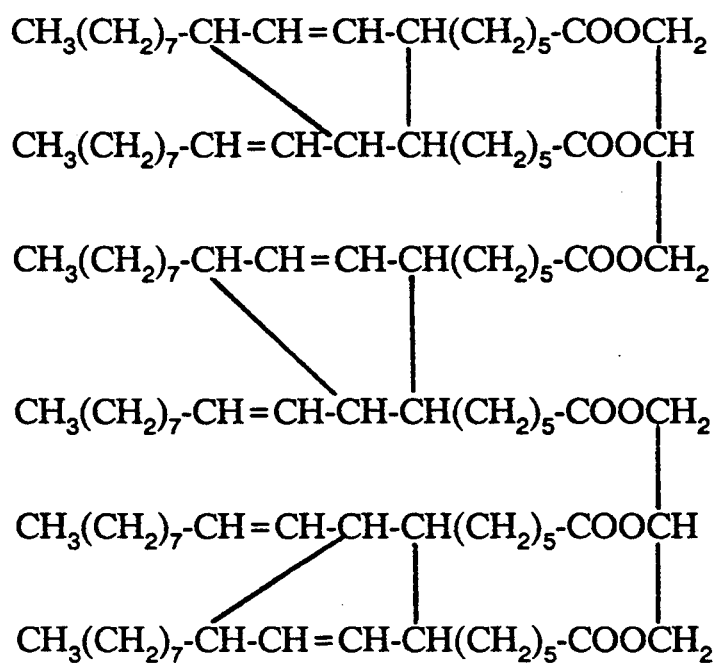
FIG. 1 shows a chemical diagram of a telomerized vegetable oil having an aliphatic ring and formed by heating in a non-oxidizing atmosphere.

The present invention relates to the discovery that telomerized vegetable oil comprising aliphatic rings and no more than 4% polyunsaturated fatty acids can be substituted for synthetic and natural (jojoba oil) vegetable wax esters in lubricant additives and lubricating compositions. The advantage of telomerized vegetable oils is that they are relatively inexpensive when compared to synthetic wax esters of the same vegetable oils because the process of telomerization requires fewer processing steps and costs for commercial manufacture. Telomerized vegetable oil derivatives can also be substituted for wax ester derivatives that are used in lubricant additives. Such derivatives include phosphite adducts of telomerized vegetable oil and sulfurized telomerized vegetable oil.

The present invention also relates to a telomerized vegetable oil produced by a process comprising heating a vegetable oil or a combination of vegetable oils to a temperature of 200° C. to 400° C. in a non-oxidizing atmosphere and in the presence of a trace water catalyst, periodically measuring viscosity of the oil over time as a measure of the telomerization reaction. The telomerization reaction is completed, by one measure, when the rate of viscosity increase over time decreases and remains constant.

The present invention further relates to a method for improving the viscosity of a lubricant additive comprising adding a telomerized vegetable oil or a sulfurized or phosphorous derivative thereof in place of a triglyceride vegetable oil or wax ester thereof. Telomerized vegetable oils have the surprising property of increasing viscosity as compared with triglyceride vegetable oils or wax esters when used as part of a lubricant additive composition or a lubricating composition. The following table compares properties of rapeseed oil (refined and degummed) with the same rapeseed oil telomerized at 300° C. for ten hours in a nitrogen atmosphere in the presence of water vapor as a catalyst.

TABLE 1

| Property | Rapeseed Oil | Telomerized Oil |
|---|---|---|
| Iodine Number | 114 | 82 |
| Viscosity @ 40° C. | 46.45 cps | 113.7 cps |
| Viscosity @ 100° C. | 10.93 cps | 18.64 cps |
| Viscosity Index | 236 | 184 |
| Specific Gravity @ 24° C. | .906 | .919 |
| Solidification Pt. | −10° C. | −4.5° C. |
| Color | light yellow | yellow |

These data for triglyceride rapeseed oil and telomerized rapeseed oil compare physical properties of this oil before and after a partial telomerization reaction. Telomerization was evidenced by a reduced iodine number at which approximately 4% of the polyunsaturated fatty acids were unreacted.

During the telomerization reaction, iodine number decreases and viscosity increases linearly with time. Either or both assays are appropriate for measuring telomerization. The following Table 2 shows a rate of formation of a telomer after 30 hours heating at 300° C. under a nitrogen blanket with water vapor.

TABLE 2

| Prop-<br>erty | Rapeseed Oil | | | | | Safflower Oil | | | | |
|---|---|---|---|---|---|---|---|---|---|---|
| | 0 | 5 hrs | 10 hrs | 20 hrs | 30 hrs | 0 | 5 hrs | 10 hrs | 20 hrs | 30 hrs |
| Iodine No. | 120 | 103 | 92 | 80 | 78 | 140 | 115 | 90 | | 54 |
| Viscosity (cs.) @ 40° C. | 541 | 927 | 1194 | 1901 | 3002 | 530 | 1090 | 2020 | | 5125 |

The telomers of both rapeseed oil and safflower oil are viscous, light-colored oils that are soluble in organic solvents and in hydrocarbon oils and esters. Some physical properties are provided in Table 3 for rapeseed oil telomer and safflower oil telomer heated under wet $N_2$ at 300° C. for 30 hours.

TABLE 3

| Property | Rapeseed Oil Telomer | Safflower Oil Telomer |
|---|---|---|
| Iodine No. | 78 | 57 |
| Kinematic viscosity | | |
| cs @ 40° C. | 301.8 | 482.9 |
| cs @ 100° C. | 38.69 | 56.41 |
| Viscosity index | 181 | 185 |
| Molecular Weight | 2700 | 3100 |

In addition to rapeseed oil, other triglyceride vegetable oils can be telomerized by the process described herein to provide a telomerized vegetable oil. For example, other appropriate vegetable oils include corn oil, crambe oil, meadowfoam oil, peanut oil, safflower oil, soybean oil and combinations thereof. The percentages of $C_{18}$, $C_{20}$ and $C_{22}$ fatty acids and the number of double bonds are listed for each vegetable oil in Table 4 below. The relative amounts of saturated, monoene, diene and triene fatty acids are shown.

TABLE 4

| | Percentages | | | | | | |
|---|---|---|---|---|---|---|---|
| | $C_{18}$ | | $C_{20}$ | | $C_{22}$ | | |
| Oil | monoene | diene | monoene | diene | monoene | diene | Sat. acid |
| Corn | 29 | 54 | | | | | 17 |
| Crambe | 62 | 31 | | | | | 7 |
| Meadowfoam | | | 62.6 | | 12.3 | 22.1 | 3.0 |
| Peanut | 62.2 | 20.6 | 1.0 | | | | 16.3 |
| Rapeseed | 76 | 11(6)* | | | | | 7 |
| Safflower | 14.4 | 66.8 | | | | | 18.8 |
| Soybean | 21.2 | 50.6(9.2)* | | | | | 19.0 |

\* - triene

Table 5 compares the iodine number of each of the triglyceride vegetable oils as starting materials before telomerization and after, 5, 6.5 or 7.5 hours of telomerization under conditions of 300° C. in a nitrogen atmosphere with a trace amount of $H_2O$. The ionization number decreases with the telomerization process.

TABLE 5

| | Iodine Number | Iodine Number After 5, 6.5, or 7.5 Hours | | |
|---|---|---|---|---|
| Oil | Starting Material | 5 | 6.5 | 7.5 |
| Corn | 99.2 | 67.1 | 61.6 | 60.3 |
| Crambe | 61.1 | 60.0 | 55.9 | 55.6 |
| Meadowfoam | 85.1 | 71.6 | 68.5 | 67.3 |
| Peanut | 71.2 | 71.0 | 70.2 | |
| Rapeseed | 100.9 | 82.2 | | |
| Safflower | 115.3 | 58.7 | 43.5 | |
| Soybean | 104.7 | 102.2 | 101.7 | 98.9 |

Table 6 shows that viscosity increases during the course of the polymerization reaction. Moreover, addition of a more polyunsaturated vegetable oil, such as linseed oil, to a vegetable oil with a lower concentration of polyunsaturated fatty acids, such as rapeseed oil, crambe oil or meadowfoam oil, results in an acceleration of the telomerication reaction. The following table lists viscosity in centistokes at 40° C. at each time.

TABLE 6

| Composition (oil) | Reaction Temp. °C. | 0 | 1 | 2 | 3 | 4 | 5 | 10 | 30 |
|---|---|---|---|---|---|---|---|---|---|
| Rapeseed (200 g) | 300 | 54.1 | — | — | — | — | 92.7 | 119.4 | 300.2 |
| Safflower (200 g) | 305 | 53.0 | — | — | — | — | 109.0 | 202.0 | 512.5 |
| Rapeseed (200 g) | 320 | 54.1 | 59.0 | 67.5 | 73.3 | 81.5 | 92.7 | — | — |
| Rapeseed (180 g) + Linseed (20 g) | 320 | 55.1 | 69.8 | 76.7 | 89.3 | 103.8 | 119.1 | — | 510.7 |
| Rapeseed (160 g) + Linseed (40 g) | 320 | 51.1 | 64.9 | 80.5 | 94.8 | 109.8 | 124.9 | — | 515.6 |

Progressive decrease in iodine number with time is a measure of the extent of telomerization. Similar monitoring of the telomerization reaction can be made by measuring increasing viscosity or increasing molecular weight as a measure of polymerization. The iodine number decreases because the number of carbon-carbon double bonds decrease with formation of aliphatic rings and, particularly cyclohexane rings between fatty acid groups. Most telomerization reactions are completed by 30 hours at 300° C. Similarly, viscosity increases as the degree of polymerization increases through formation of aliphatic rings.

These data comparing physical properties of several triglyceride vegetable oils versus its telomerized counterpart show a reduced iodine number or an increased viscosity at which approximately 4% of the polyunsaturated fatty acids were unreacted. These data show reduced iodine numbers for rapeseed oil, in addition to other vegetable oils, such as crambe oil, corn oil, peanut oil, meadowfoam oil, soybean oil, and safflower oil.

In a preferred embodiment, the starting vegetable oil is a combination of a triglyceride vegetable oil having a lower polyunsaturated fatty acid content in the about 10% to 25% range (e.g., rapeseed oil, meadowfoam oil, crambe oil) and a triglyceride vegetable oil having a higher polyunsaturated fatty acid content of more than 50% (e.g., corn oil, linseed oil). Addition of a higher polyunsaturated vegetable oil accelerates the telomerization reaction, allowing a completion of the reaction (defined as a plateau in a viscosity versus time curve) faster with processing and energy cost savings.

Rapeseed oil is a triglyceride vegetable oil containing about 15% to 25% polyunsaturated fatty acids. The degree of unsaturation and percentage of polyunsaturation depends upon crop growing conditions. These polyunsaturates are mainly linoleic and linolenic acids and are the source of a problem of oxidative instability of vegetable oils. The telomerization process heats the vegetable oil from about 200° C. to about 400° C. in a non-oxidizing atmosphere (preferably a reducing atmosphere, such as nitrogen) in the presence of trace amounts of water as a catalyst, to cause the polyunsaturated fatty acids to form monounsaturated polymers containing aliphatic rings. This, in essence, polymerizes the triglycerides without separating the fatty acid component from the glycerol backbone. An example of the reaction product chemical configuration is shown in FIG. 1. The resulting telomerized vegetable oil displays characteristics of reduced iodine number reflecting the fact that 4% or less of the fatty acids are polyunsaturated, the presence of aliphatic rings connecting fatty acid chains of different triglyceride molecules, a significant reduction of the viscosity index, and increased oxidative stability.

The process of telomerization of a vegetable oil comprises heating a crude, partially purified or purified vegetable oil at a temperature of from about 200° C. to about 400° C. from about 6 to about 40 hours in a non-oxidizing atmosphere. Preferably a reducing atmosphere is used with a gas selected from the group consisting of nitrogen, helium, argon, neon, and combinations thereof. Most preferably, a trace amount of water is added to facilitate the telomerization process. The amount of telomerization is determined by periodically measuring the iodine number or viscosity of the vegetable oil, and when the telomerized oil's iodine number indicates less than 4% polyunsaturated fatty acids or viscosity increases at a decreased rate, the telomerization process is complete. Preferably, the iodine number drop indicates less than 2% polyunsaturated fatty acids.

One can determine the percentage of polyunsaturated fatty acids by first determining the amount of polyunsaturated fatty acids in the triglyceride vegetable oil and then determining the projected final iodine number by the following formula:

$$\sum_{i=1}^{i=1} W_i I_i$$

where $I_i$ is the iodine number of the ith fatty acid, $W_i$ is the weight percentage of the ith fatty acid and n is the total number of saturated, monoenoic and telomerized fatty acids plus the remaining polyunsaturated fatty acids. This formula determines the projected final iodine number of a telomerized oil. Iodine number is measured by determining the grams of iodine absorbed by 100 grams of an oil. For example, iodine number is determined by adding 0.5 g of the oil, 10 ml of carbon tetrachloride and 25 ml of iodine solution (Wisz Reagent) and incubated for one hour in the dark at room temperature. After incubation, the reaction is stopped by addition of 10 ml of 15% (w/w) potassium iodide solution and 100 ml of water. This solution is titrated with 0.10 N sodium thiosulfate until the yellow color essentially disappears. At that point, 4 drops of a starch solution is added to form a dark blue color. Titration with sodium thiosulfate continues until the solution exhibits a clear or white end product. The iodine number (I) is calculated by the following equation:

$$I = \frac{[(\text{ml to titrate blank}) - (\text{ml to titrate sample})] (0.10)(12.7)}{(\text{\# of grams of sample})}$$

The iodine number of a triglyceride oil is a combination of the iodine number of polyunsaturated (e.g., diunsaturated) components and monounsaturated components. Prior to the telomerization process, a vegetable oil with many polyunsaturated fatty acids will have a relatively high iodine number because a diunsaturated fatty acid reacts with four atoms of iodine (two moles of $I_2$), whereas a monounsaturated fatty acid will react with two atoms of iodine (one mole of $I_2$). As telomerization proceeds, diunsaturated fatty acids form aliphatic ring structures with other diunsaturated fatty acids and are converted to saturated or monounsaturated components. Thus, the iodine number decreases because the number of double bonds decreases. At completion of telomerization, the iodine number becomes the same as that of a monounsaturated triglyceride oil.

For example, if the starting triglyceride vegetable oil had an iodine number of 110 and it contained a mixture of trioleylglyceride and trilinoleylglyceride, the projected completion of telomerization yields an iodine number of about 72, because the iodine number of trioleylglyceride is about 82. The iodine number of trilinoleylglyceride is about 174. Thus, the original triglyceride vegetable oil mixture must have contained about 30% trilinoleylglyceride and 70% trioleylglyceride. The sum of 70% of 82 plus 30% of 174 is about 110, or the iodine number of the starting triglyceride vegetable oil.

Another method for monitoring the telomerization process is to determine the viscosity of the telomerized oil at a particular temperature. Viscosity increases as the triglycerides polymerize and molecular weight increases. Therefore it is also possible to monitor viscosity at a particular temperature to determine when the telomerization reaction has produced less than 4% polyunsaturated fatty acids because the relationship between viscosity, molecular weight and amount of polyunsaturated fatty acids remaining after formation of aliphatic rings is proportional. The telomerization reaction is complete when viscosity versus time plateaus or increases at a lower rate.

Corn, crambe, meadowfoam, peanut, rapeseed and soybean oils were telomerized at 300° C. for 7.5 hours as described herein. Viscosity at 40° C. for each oil was compared before and after telomerization. The following Table 7 shows the results.

TABLE 7

| Vegetable Oil | Viscosity at 40° C. in cs | |
|---|---|---|
| | Triglyceride | Telomerized |
| Corn | 34 | 2365 |
| Crambe | 49 | 103 |
| Meadowfoam | 54 | 63 |
| Peanut | 36 | 33 |
| Rapeseed | 44 | 259 |
| Soybean | 29 | 44 |

Moreover, as the fatty acids telomerize through formation of aliphatic rings, the molecular weight of the telomerized vegetable increase to a molecular weight of about 2000 to about 5000 daltons.

Aliphatic ring structures, such as cyclohexane rings, have a higher refractive index than linear compounds of the same molecular weight. Thus an increase in refractive index indicates the formation of aliphatic rings and telomerization of the vegetable oil. Table 8 illustrates a comparison of refractive index for various vegetable oils before and after telomerization at 300° C. for 7.5 hours.

TABLE 8

| Vegetable Oil | Refractive Index | |
|---|---|---|
| | Triglyceride | Telomerized |
| Corn | 1.4765 | 1.4776 |
| Crambe | 1.4734 | 1.4742 |
| Meadowfoam | 1.4735 | 1.4737 |
| Peanut | 1.4721 | 1.4725 |
| Rapeseed | 1.4740 | 1.4742 |
| Safflower | 1.4785 | 1.4794 |
| Soybean | 1.4766 | 1.4770 |

Addition of a telomerized vegetable oil, according to the present invention, can function as a thickening agent for thickening and cross-grading lubricating oils, and particularly for sheer stable derivatives. Thus, a telomerized vegetable oil can function as a low molecular weight polymer with additional thermal oxidative stability characteristics. We added 2%, 4%, and 8% telomerized rapeseed oil to a base fluid having a 79% VI (viscosity index). As shown in Table 9, addition of telomerized rapeseed oil improved viscosity of a low VI oil.

TABLE 9

| | Base Fluid | 2% Telomer | 4% Telomer | 8% Telomer |
|---|---|---|---|---|
| Viscosity (cs @ 40° C.) | 21.37 | 21.67 | 21.98 | 22.62 |
| Viscosity (cs @ 100° C.) | 4.03 | 4.26 | 451 | 5.02 |
| Viscosity Index | 79 | 98 | 117 | 116 |

The telomerization process is conducted in a non-oxidizing atmosphere. Preferably it is conducted with a minimum amount of oxygen present, and most preferably under a nitrogen blanket. Other reducing atmospheres can be used, such as the inert gases helium, neon, argon and combinations thereof.

Preferably, a catalyst at a concentration from about 0.5% to about 5.0% by weight, is added to the triglyceride vegetable oil for the telomerization reaction. The catalyst is a cationic catalyst, anionic catalyst, solid strong acid catalyst or a combination thereof. Examples of cationic catalysts include ester-complexed chloride, phenol-complexed boron trifluoride and dibutyl tin dichloride. Anionic catalysts include, for example, butyl lithium, butyl potassium, and metallic sodium. Examples of solid acid catalysts include Zeolites and resin sulfonic acid.

Preferably, a reaction initiator may be added to the vegetable oil to start the telomerization process. An example of a reaction initiator is a peroxide, such as di-t-butyl-peroxide or air, at concentrations ranging from about 1.0% to about 10% by weight.

Vegetable oil for the telomerization process is a triglyceride vegetable oil comprising from about 10% to about 80% polyunsaturated fatty acids. At least 90% of the fatty acids should be from about 16 to about 26 carbon atoms in length with few, if any, branched chains. Preferably, the triglyceride vegetable oil contains from about 18 to about 22 carbon atoms in 90% of its fatty acids and from about 10% to about 25% of its fatty acids are polyunsaturated. Preferred vegetable oils that have this amount of polyunsaturated fatty acids are rapeseed oil, crambe oil, and meadowfoam oil. Other appropriate vegetable oils include, for example, soya bean oil, peanut oil, safflower oil, sunflower seed oil, cotton seed oil, olive oil, corn oil, coconut oil, palm oil, combinations thereof and the like.

Telomerized vegetable oil is further characterized by increased oxidation resistance. Increased oxidation resistance, or oxidative stability, results from polymerization of the vegetable oils. There are fewer carbon-carbon double bonds in telomerized vegetable oil subject to attack by oxygen. For example, when refined rapeseed oil (iodine number 114) was compared with telomerized rapeseed oil (iodine number 82) for thermal oxidative stability, viscosity increase due to oxidation damage was only 25% for the telomerized oil versus 67% for the triglyceride rapeseed vegetable oil. Each oil was heated to 121° C. and injected with 50 cc/min of air over a period of 24 hours. These data indicate that the oxidative resistance of the telomerized oil is significantly increased over the same oil prior to telomerization.

Another oxidative stability comparison was made with rapeseed oil, telomerized rapeseed oil, jojoba oil (a natural wax ester) and several synthetic commercial wax esters, often derived from rapeseed oil. Viscosity at 100° C. was compared before air injection and after 24 hours of air injection as described above. The following Table 10 describes the results:

TABLE 10

| Sample (Iodine No.) | Viscosity (0) | Viscosity (24) | % Change |
|---|---|---|---|
| rapeseed oil (114) | 10.93 cps | 18.22 cps | 66.7 |
| telomerized (82) | 18.64 cps | 23.38 cps | 25.4 |
| jojoba oil (82) | 6.05 cps | 8.52 cps | 40.8 |
| SWEA | 5.83 cps | 8.43 cps | 44.6 |
| SWEB | 6.00 cps | 7.96 cps | 32.7 |
| SWEC | 4.69 cps | 6.43 cps | 37.1 |

SWEA, SWEB, and SWEC are liquid synthetic wax esters of rapeseed oil. These data show increased oxidative resistance as a result of the telomerization process.

Telomerized vegetable oil can be used as part of a lubricant additive alone, and derivatives can be made from telomerized vegetable oil, including phosphite adducts and sulfurized telomerized vegetable oils. Sulfurized derivatives of telomerized vegetable oils are made by known techniques of sulfurization. For example, 20 grams of telomerized rapeseed oil, as described herein, was sulfurized with 1 gram of sulfur at 180° C. for two hours under nitrogen with stirring. The resulting sulfurized telomerized rapeseed oil was soluble at a 5% concentration in mineral oil and had a 2B score in a copper strip test. Similarly, 20 grams of telomerized meadowfoam oil was sulfurized with 3 grams of sulfur under the same conditions. The resulting sulfurized oil was soluble in mineral oil at a 5% concentration and provided a score of 2A in the copper strip test.

A phosphite adduct of a telomerized vegetable oil is formed by the reaction product of a telomerized vegetable oil and a compound of the formula:

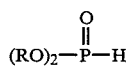

$$(RO)_2-\overset{O}{\underset{\|}{P}}-H$$

wherein R is H, $C_{1-12}$ alkyl, $C_{1-12}$ aryl, $C_{1-12}$ alkaryl, $C_{1-12}$ aralkyl, or cyclo $C_{4-8}$ alkyl. Preferably, R is $C_{4-8}$ alkyl, $C_{4-8}$ aryl, $C_{4-8}$ alkaryl, $C_{4-8}$ aralkyl, or cyclo $C_{4-8}$ alkyl. Most preferably, R is n-butyl. Telomerized vegetable oils do not have as many available carbon-carbon double bonds as triglyceride vegetable oils. As the phosphorous compound attaches to a carbon-carbon double bond, not as much phosphorous can be reacted to a telomerized oil as compared with its triglyceride vegetable oil counterpart. Accordingly, it is within the scope of the present invention to add a phosphite adduct of a natural wax ester (e.g., jojoba oil) as described in U.S. Pat. No. 4,873,008, and/or a phosphite adduct of a synthetic wax ester or triglyceride oil as described in U.S. Pat. No. 4,970,010.

The present invention further relates to lubricating compositions, comprising a lubricant additive and a lubricant base, (e.g., mineral oil) appropriate for its intended use. Examples of lubricant bases include hydrocarbon oil, synthetic hydrocarbon, mineral oil, an ester-base, a mixture of mineral oil and an ester base, a mineral oil-based grease, petroleum HVI, MVI and LVI, and a synthetic hydrocarbon-based grease. Specific examples can be found in standard text books and in, for example, U.S. Pat. No. 4,873,008.

Depending upon the application and the desired extent of antiwear protection, the total lubricant additive concentration within the lubricating composition will be from about 0.1% to about 60% by weight. The lubricant additive of the present invention comprises at least a telomerized vegetable oil and possibly a sulfurized derivative or a phosphite adduct of a triglyceride vegetable oil, a vegetable oil wax ester or a telomerized vegetable oil. The lubricant additive comprises at least one telomerized component from the three groups of components, wherein the three components are telomerized vegetable oil, telomerized and sulfurized vegetable oil or a sulfurized wax ester, and phosphite adduct of telomerized vegetable oil. Preferably, a lubricant additive comprises telomerized vegetable oil, a telomerized and sulfurized vegetable oil, and a phosphite adduct of a wax ester.

The amount of telomerized component in the lubricant additive will vary depending on the extent of antiwear protection desired and the desired viscosity of the final lubricating composition. More telomerized vegetable oil will be substituted for a wax ester or a triglyceride vegetable oil if greater viscosity is needed and more cost savings are needed. Moreover, sulfurized wax ester will be used in more viscous lubricating compositions, such as greases and hydraulic oils which will also contain a relatively higher concentration of telomerized vegetable oil. Moreover, a cutting oil or a metal working lubricant will comprise a telomerized vegetable oil, a sulfurized wax ester and a phosphite adduct of either a telomerized vegetable oil, a vegetable oil, or a synthetic wax ester.

Different combinations and concentrations of the lubricant additive will depend upon the desired product attributes. For example, a hydraulic oil will have a lubricant additive comprising (percentages are by weight of the total composition) a relatively low concentration (about 0.1% to about 0.5%) of a sulfurized wax ester, a relatively high concentration of telomerized vegetable oil (from about 2% to about 5%), and a relatively low concentration of a phosphite adduct of a wax ester or a telomerized vegetable oil (from about 0.1% to about 0.6%). A metal cutting oil, for example, will have a lubricant additive comprising approximately 7% sulfurized wax ester, about 1% to about 4% telomerized vegetable oil and very little, if any, phosphite adduct of a wax ester or a telomerized vegetable oil. An automobile engine oil, for example, will contain a lubricant additive comprising approximately 1% sulfurized wax ester, approximately 2% telomerized vegetable oil, and approximately 2% of a phosphite adduct of a telomerized vegetable oil and/or a wax ester, and other additives as are normally used in an automobile engine oil.

The following examples illustrate the frictional characteristics of a particular telomerized vegetable oil derivative compared with standard lubricant additives. These examples illustrate the properties of inventive compositions and do not limit the scope of the present invention.

EXAMPLE 1

This example illustrates a comparison of coefficient of friction using a low viscosity friction apparatus (LVFA). Three dibutyl phosphite adduct oil derivatives were tested, including (a) a triglyceride rapeseed oil, (b) a wax ester of rapeseed oil, and (c) a telomerized rapeseed oil as the inventive derivative. Each of the three oils was reacted with equal amounts of dibutyl phosphorous as described herein. One percent or two percent (by weight) phosphite adduct was added to 338 base stock to form each of the test lubricating compositions. The 338 base stock is a solvent refined mineral oil. The LVFA test was conducted at two sliding speeds, 5 feet per minute and 15 feet per minute, at a temperature of 250° F., pressure of 240 psi, and SAE 1020 steel on steel. The results are as follows:

| Composition (phosphite adduct) | Average speed | % Reduction |
|---|---|---|
| Sliding Speed 5 Ft/Min Coefficient of Friction | | |
| Base fluid control | 0.0805 | |
|  | 0.0801 | |
|  | 0.0800 | |
| Base + 1% ester | 0.0695 | 14 |
| Base + 2% ester | 0.0645 | 21 |
| Base + 1% triglyceride | 0.0732 | 9 |
| Base + 2% triglyceride | 0.0698 | 13 |
| Base + 1% telomerized | 0.0726 | 10 |
| Base + 2% telomerized | 0.0699 | 13 |
| Sliding Speed 15 Ft/Min Coefficient of Friction | | |
| Base fluid control | 0.0842 | |
|  | 0.0823 | |
|  | 0.0855 | |
| Base + 1% ester | 0.0724 | 14 |
| Base + 2% ester | 0.0671 | 20 |
| Base + 1% triglyceride | 0.0752 | 9 |
| Base + 2% triglyceride | 0.0728 | 12 |
| Base + 1% telomerized | 0.0778 | 9 |
| Base + 2% telomerized | 0.0752 | 12 |

These data show that the frictional properties of the dibutyl phosphite adduct of telomerized vegetable oil are similar to the dibutyl phosphite adduct of triglyceride vegetable oil. However, the dibutyl phosphite adduct of a wax ester of vegetable oil displayed somewhat better frictional properties.

EXAMPLE 2

This example illustrates a comparison of limited slip additive formulations in a testing model to measure chatter in a SRD Wheel Roller Test in a Pontiac TransAm Rear Axle. Three limited slip additives were prepared and added to a Texaco 80W-90 base fluid. The Texaco 80W-90 base fluid is a reference point that provides chatter in a 1982 Pontiac TransAm rear axle.

Testing procedure involved: (1) removing differential internal components in a 1982 Pontiac TransAm; (2) reassembling differential with Texaco 80W-90 base fluid; (3) flushing rear axle housing and components and installing differential; (4) filling sump with base fluid; (5) driving at least 20 miles for breaking in rear axle; (6) performing a left and right rear wheel roller for 2–4 min. to determine dynamic thrust; (7) adding a limited slip additive to rear axle sump; (8) driving five miles to circulate the additive; (9) determining left and right well dynamic thrust; (9) elevating sump temperature to 250° F. on wheel rollers to evaluate chatter; and (10) raising the sump temperature higher if no chatter was heard at 250° F. Approximately 4 oz. of each test limited slip additive was added to the test system differential.

Test formulation 1 comprised (all percentages are by weight) 60% of a N-dibutyl phosphite adduct of a rapeseed oil synthetic wax ester, 10% of a rapeseed oil wax ester, and 30% polyalpha olefin (4cs viscosity). Test formulation 2 comprised 60% of a N-dibutyl phosphite adduct of telomerized rapeseed oil (2 moles phosphite adduct added to 1 mole of telomer), 30% polyalpha olefin (4 cs viscosity) and 10% telomerized rapeseed oil. Test formulation 3 comprised 60% of a N-dibutyl phosphite adduct of a rapeseed oil synthetic wax ester, 10% of a rapeseed oil synthetic wax ester and 30% of petroleum HVI (high viscosity index) neutral oil (about 500 VI).

Only test formulation 2, containing a telomerized oil and a telomerized derivative, failed to produce chatter the under severe testing conditions. The following Table 10 illustrates this comparison:

TABLE 11

| Test Formulation | Chatter Rating | Bias Reduction % |
| --- | --- | --- |
| 1 | Chatter 8 @ 250° F. sump | 29% |
| 2 | No chatter @ 280° F. sump | 13%/19% |
| 3 | Chatter 7/8 @ 250° F. sump | 23%/27% |

A limited slip additive made with telomerized oils, according to the present invention, eliminated a chatter problem in a rear axle test system that could not be addressed by conventional limited slip additives.

What is claimed is:

1. A phosphite adduct of a telomerized vegetable oil comprising a mono-, di-, or tri-adduct of the reaction product of a telomerized vegetable oil and:

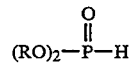

wherein R is selected from the group consisting of H, $C_{1-12}$ alkyl, $C_{6-12}$ aryl, $C_{6-12}$ alkaryl, $C_{6-12}$ aralkyl, and cyclo $C_{4-8}$ alkyl.

2. The phosphite adduct of a telomerized vegetable oil according to claim 1 wherein R is selected from the group consisting of $C_{4-8}$ alkyl, $C_{6-8}$ aryl, $C_{6-8}$ alkaryl, $C_{6-8}$ aralkyl, and cyclo $C_{4-8}$ alkyl.

3. The phosphite adduct of a telomerized vegetable oil according to claim 2 wherein R is a butyl group.

4. A lubricant additive comprising a telomerized vegetable oil and the phosphite adduct of telomerized vegetable oil according to claim 1.

5. The lubricant additive of claim 4 wherein the phosphite adduct derivative is a reaction product of the telomerized vegetable oil, synthetic wax ester, and/or triglyceride vegetable oil and:

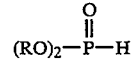

wherein R is selected from the group consisting of H, $C_{1-12}$ alkyl, $C_{6-12}$ aryl, $C_{6-12}$ alkaryl, $C_{6-12}$ aralkyl, and cyclo $C_{4-8}$ alkyl.

* * * * *